United States Patent
Longo et al.

(10) Patent No.: US 8,747,438 B2
(45) Date of Patent: Jun. 10, 2014

(54) SUTURE THREAD

(75) Inventors: Maurizio Longo, Rome (IT); Federica Scacchia, Teramo (IT); Francesco Lazzaro, L'aquila (IT); Feliciano Crovella, Naples (IT)

(73) Assignee: Assut Europe S.p.A., Rome (RM) (IT)

( * ) Notice: Subject to any disclaimer, the term of this patent is extended or adjusted under 35 U.S.C. 154(b) by 0 days.

(21) Appl. No.: 13/807,922

(22) PCT Filed: Jul. 7, 2011

(86) PCT No.: PCT/IB2011/053016
§ 371 (c)(1),
(2), (4) Date: Dec. 31, 2012

(87) PCT Pub. No.: WO2012/004758
PCT Pub. Date: Jan. 12, 2012

(65) Prior Publication Data
US 2013/0103078 A1    Apr. 25, 2013

(30) Foreign Application Priority Data
Jul. 8, 2010 (IT) .............................. RM2010A0373

(51) Int. Cl.
*A61L 17/00* (2006.01)
(52) U.S. Cl.
USPC ........................................................ 606/228
(58) Field of Classification Search
USPC .................................. 606/222–225, 228–233
See application file for complete search history.

(56) References Cited

U.S. PATENT DOCUMENTS

| | | | |
|---|---|---|---|
| 5,102,418 A * | 4/1992 | Granger et al. ................ | 606/224 |
| 6,506,197 B1 | 1/2003 | Rollero et al. | |
| 6,596,014 B2 | 7/2003 | Levinson et al. | |
| 2001/0051236 A1* | 12/2001 | Kido et al. .................... | 428/34.1 |
| 2003/0149447 A1 | 8/2003 | Morency et al. | |
| 2005/0267531 A1* | 12/2005 | Ruff et al. ...................... | 606/228 |
| 2006/0116718 A1* | 6/2006 | Leiboff ......................... | 606/228 |
| 2009/0248067 A1 | 10/2009 | Maiorino | |

FOREIGN PATENT DOCUMENTS

WO    WO 97/09935 A1    3/1997
WO    WO 2005/016176 A2    2/2005

OTHER PUBLICATIONS

International Search Report for PCT/IB2011/053016 filed Jul. 7, 2011 in the name of ASSUT EUROPE S.p.A. Mail Date: Sep. 21, 2011.
Written Opinion of the ISA for PCT/IB2011/053016 filed Jul. 7, 2011 in the name of ASSUT EUROPE S.p.A. Mail Date: Sep. 21, 2011.
Written Opinion of the IPEA for PCT/IB2011/053016 filed Jul. 7, 2011 in the name of ASSUT EUROPE S.p.A. Mail Date: Jul. 2, 2012.
International Preliminary Report on Patentability of the IPEA for PCT/IB2011/053016 filed Jul. 7, 2011 in the name of ASSUT EUROPE S.p.A. Mail Date: Oct. 1, 2012.

* cited by examiner

*Primary Examiner* — Ashley Fishback
(74) *Attorney, Agent, or Firm* — Steinfl & Bruno, LLP

(57) ABSTRACT

A suture thread having: a thread-shaped main body with spikes and a stopper cylinder having a diameter enlarged with respect to the main body is described.

1 Claim, 3 Drawing Sheets

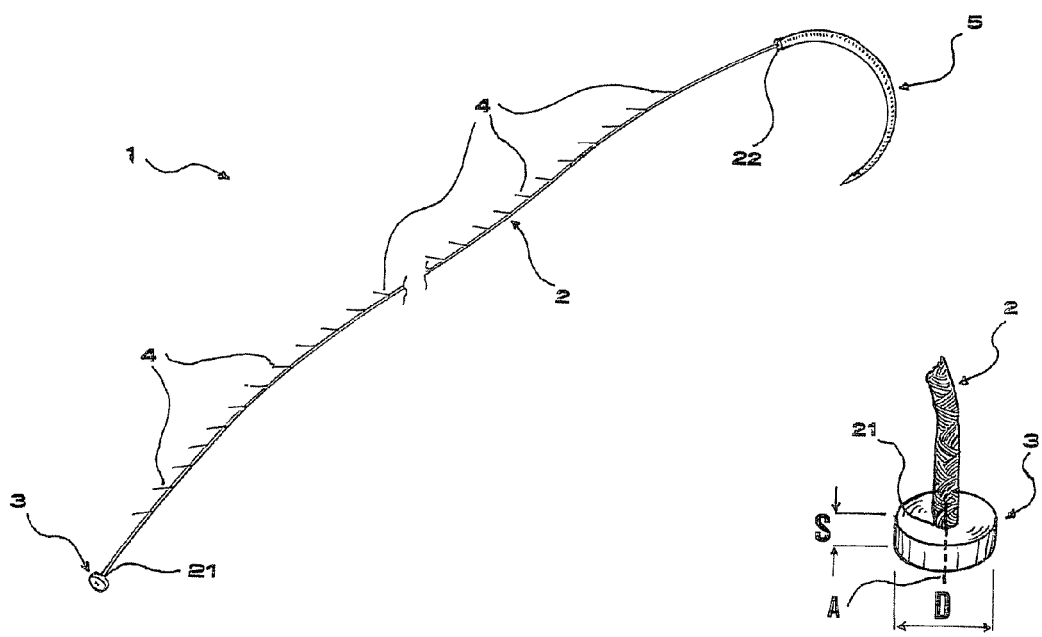
FIG.1
FIG.1A
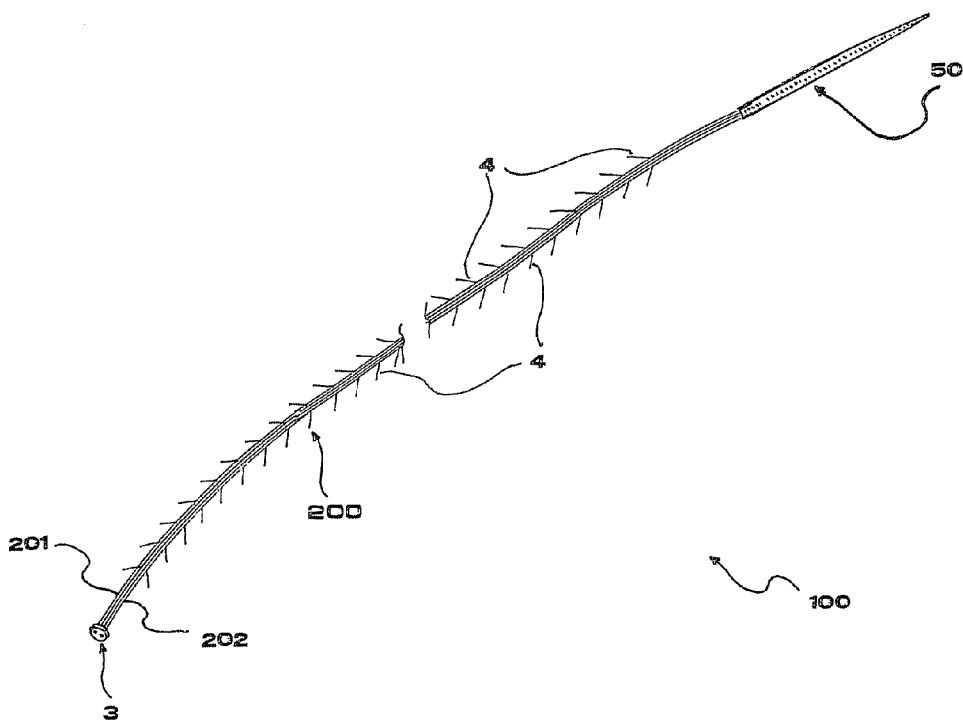
FIG.2

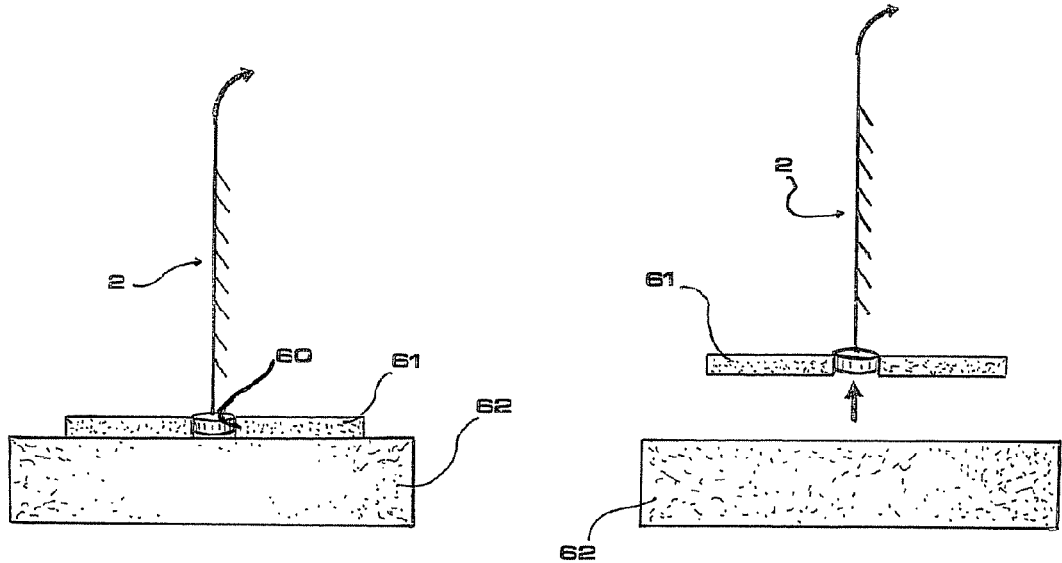
FIG.4A
FIG.4B
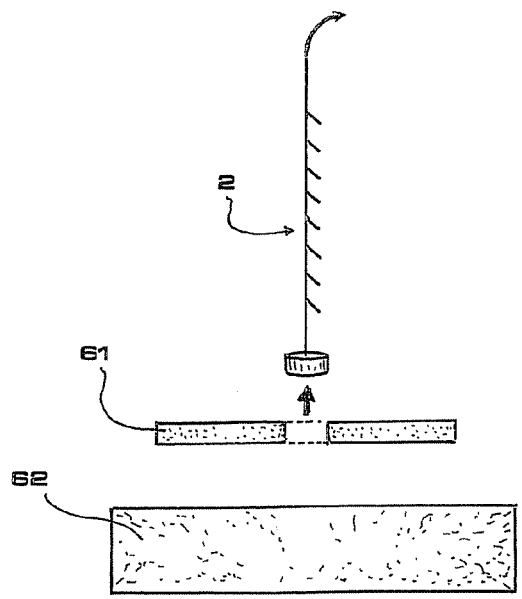
FIG.4C

SUTURE THREAD

CROSS REFERENCE TO RELATED APPLICATIONS

The present application is the US national stage entry of International Application PCT/IB2011/053016 filed on Jul. 7, 2011, which in turn claims priority to Italian Application RM2010A000373 filed on Jul. 8, 2010.

The present invention refers to a thread, especially for use as a suture thread.

The operation of surgical nature most frequently performed in operating room and outpatient clinic surgery is certainly that of suturing by thread. In spite of the frequency and the "historicity" of use of the suture threads, the in situ blocking modes of the ends thereof have not been optimized yet. In particular, in order to secure one end of the thread against a portion of biological tissue, the same thread is generally knotted on itself.

However, this blocking mode is intrinsically less than reliable as the knot, over time, tends to come undone; this entails that, for each suturing operation that proves necessary during surgery, the operator is forced to make a high number of knots in sequence. Therefore, the entire suturing operation carried out through the knotting technique requires a non-negligible time significantly affecting the total length of the intervention, with the associated consequences for the patient's well-being.

Therefore, the technical problem set and solved by the present invention is that of providing a thread—and in particular a suture thread—allowing to overcome the drawbacks mentioned above with reference to the known art.

Such a problem is solved by a thread according to claim 1.

Preferred features of the present invention are set forth in the dependent claims thereof.

The present invention provides some relevant advantages. The main advantage lies in the fact that the thread of the invention, by being equipped with a stopper included in correspondence of a longitudinal end of the thread itself, allows to reduce surgical times, eliminating the need to make plural knots, and concomitantly improving the reliability of the sutures, since the block is not subject to the drawback of coming undone. Moreover, by eliminating the need to knot the main body of the thread on itself, the invention allows a greater variety of choice for the rigidity level of the latter and for the materials of which it is made, thereby allowing to meet any type of suturing and surgery need.

Other advantages, features and operation steps of the present invention will be made apparent in the following detailed description of some embodiments thereof, given by way of example and not for limitative purposes. Reference will be made to the figures of the annexed drawings, wherein:

FIG. 1 shows a perspective view of a first preferred embodiment of the suture thread according to the present invention;

FIG. 1A shows an enlarged view of a detail of the thread of FIG. 1;

FIG. 2 shows a perspective view of a second preferred embodiment of the suture thread according to the present invention;

FIGS. 4A, 4B and 4C show schematic front views illustrating three respective steps of a preferred method for manufacturing the suture thread of FIG. 1.

Figure 3:
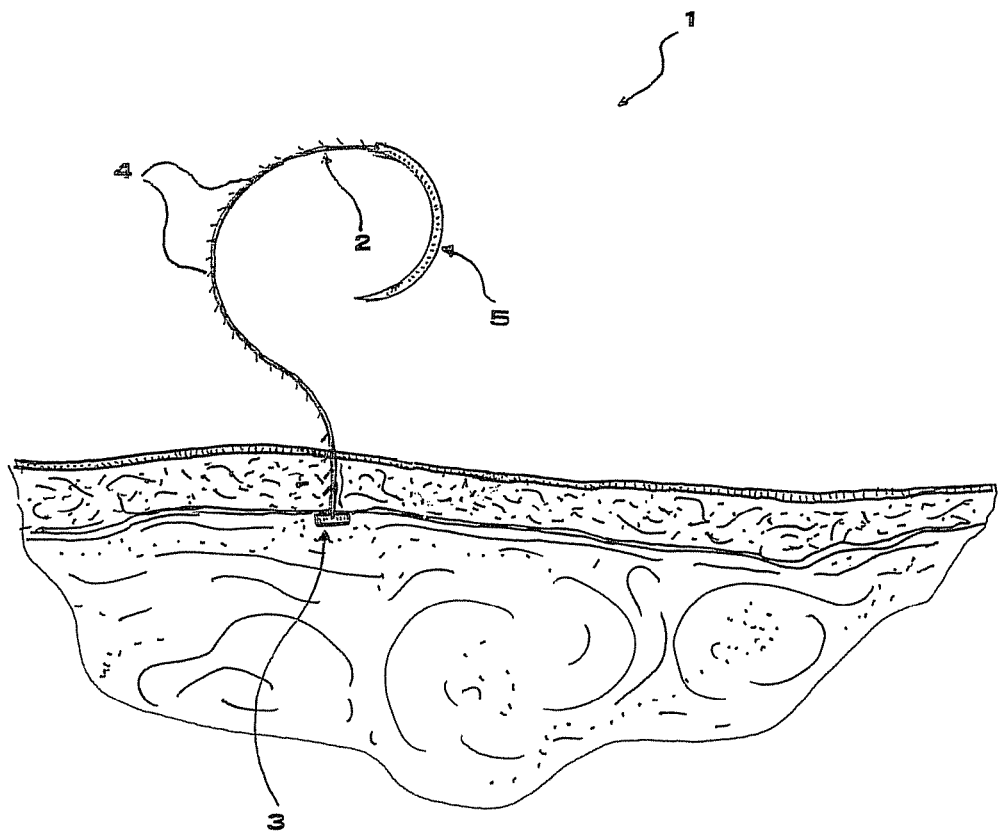
FIG. 3 shows a perspective view of the suture thread of FIG. 1, in is use during surgery.

Referring initially to FIGS. 1 and 1A, a suture thread according to a first preferred embodiment of the invention is generally denoted by 1.

The thread 1 comprises first of all an elongated main body 2 having just a thread-like shape. The main body 2 is preferably flexible and extends, in a straight and extended configuration, along a longitudinal axis A.

On the main body 2 there are preferably provided holding spikes 4, i.e. thread portions arranged obliquely with respect to the prevalent direction of development of the main body 2 and apt, by virtue of said tilt, to engage the tissue sutured by the thread itself so as to prevent the unthreading of the latter along a given pull direction. Also the length and the thickness of the spikes 4 can be selected depending on the selected cutting tilt.

The spikes 4 can be applied on the main body 2 in a monolateral way, as in the depicted example, or in a plurilateral way. In both cases they can be manufactured in a monodirectional way, as in the depicted example, or in a pluridirectional way, i.e. have a tilt along a single direction or along plural divergent directions. Moreover, the spikes 4 can be applied on the main body 2 even along a helical path or a spiral-like path.

In correspondence of a first longitudinal end 21 of the main body 2, the thread 1 provides a stopper 3 having a section enlarged with respect to the main body 2 itself.

Preferably, the stopper 3 has a substantially cylindrical shape, preferably with an axis of the cylinder aligned with the axis A of the main body 2.

Always according to a preferred embodiment, the stopper 3 has a diameter D of about 4 mm and a thickness S comprised in a range of about 1-2 mm.

During suturing, and as shown in FIG. 3, the stopper 3, by virtue of its own section enlarged with respect to the main body 2, can block the corresponding longitudinal end 21 of the latter in abutment against a tissue flap.

Main body 2 and stopper 3 can be made both of a same material and of different materials, preferably of absorbable synthetic type.

In the present example, the stopper 3 and/or the main body 2 can be made of a material selected from a group comprising: glycolide polymer (PGA), copolymer of glycolide and lactide (PGLA), Poly(p-dioxanone) (PDO), copolymer of glycolide and epsilon-caprolactone (PGCL), and copolymer of Poly(l-lactide) and epsilon-caprolactone P(LA-CL).

The stopper 3 can be fixed to the main body 2 by heat-sealing.

In particular, a preferred embodiment schematically illustrated in FIGS. 4A, 4B and 4C envisages that the stopper 3 be made by melting of poly(p-dioxanone) polymer in suitable moulds 60 of cylindrical shape of the above-mentioned dimensions, preferably made in the form of openings shaped on a metal plate 61 resting on a board 62 heated to about 130° C.

The connection between stopper 3 and main body 2 is then obtained by the following steps:

sealing of the "free" end 21 of the thread into the polymer paste still molten in the mould 60 (the correct positioning of the thread at the center of the cylindrical element can be guaranteed by a truing device positioned on the plate 61)—this step is schematically shown in FIG. 4A;

removing the metal plate 61 from the heated board 62, in order to obtain the cooling of the plate itself—this step is schematically shown in FIG. 4B; and separating the stopper from the metal plate—this step is schematically shown in FIG. 4C.

Advantageously, the thread 1 is then prearranged, in correspondence of a second longitudinal end 22 of the main body 2 opposite to that associated to the stopper 3, with a suture needle 5 having a substantially straight or curved shape. Such a needle can be made of stainless steel (e.g. AISI 300 series or AISI 400 series).

According to a second preferred embodiment shown in FIG. 2, a suture thread, denoted herein by 100, has a main body, denoted herein by 200, which comprises a pair of thread-shaped members 201, 202, apt to define a generally ring-shaped or loop-like structure of the thread itself.

The thread 100 comprises a stopper 3 analogous to that already described above, and in this case as well it is prearranged with a suture needle, here substantially straight, denoted by 50.

It will be understood that a plurality of suture threads, each as described above with reference to FIGS. 1 and 2, may be provided in various calibers, preferably comprised in the range USP 6/0-8, and in various lengths.

It will also be understood that a plurality of suture threads, each as described above with reference to FIGS. 1 and 2, may be provided in the form of a reel. In particular, in that case threads will be arranged in a longitudinal sequence and removably connected in correspondence of respective ends.

It will be understood that although the invention has been described with specific reference to suture applications, it can advantageously be used for any type of surgical need in which the use of a thread to be blocked in situ be required.

Moreover, in a broader meaning the invention can find application also in a field different from the surgical one, for instance that of threads for sewing, especially in specialized fields like those of sewing or stitching technical fabrics, such as for use in fishing, motorcycling, etc.

The present invention has been hereto described with reference to preferred embodiments thereof. It is understood that other embodiments might exist, all falling within the concept of the same invention, as defined by the protective scope of the claims hereinafter.

The invention claimed is:

1. A method for manufacturing a thread comprising:

an elongated main body having a plurality of holding spikes; and a stopper having a section enlarged with respect to said main body and arranged at a longitudinal end of the main body to block said end in abutment against a tissue flap, wherein said stopper has a substantially cylindrical shape, with an axis of the cylinder aligned with a direction of longitudinal development of said main body, wherein said stopper has a thickness along said cylinder axis comprised in a range of about 1-2 mm, wherein said stopper has a diameter of about 4 mm, and wherein said stopper and said main body are made of a material selected from a group comprising: glycolide polymer (PGA), copolymer of glycolide and lactide (PGLA), Poly(p-dioxanone) (PDO), copolymer of glycolide and epsilon-caprolactone (PGCL), and copolymer of Poly(l-lactide) and epsilon-caprolactone P(LA-CL), the method comprising the steps of:

providing the main body of the thread having a plurality of holding spikes;

providing a mould having a shape corresponding to that of said stopper, in the form of a seat obtained in a plate, wherein said plate rests on a board apt to be heated;

melting inside said mould a selected material for manufacturing said stopper by heating said board;

heat-welding said main body to said stopper by inserting one end of said main body into said molten material and by subsequently cooling the assembly, this latter step performed by removing said plate from said heated board; and separating said stopper from said plate.

* * * * *